United States Patent [19]

Schmitz

[11] 4,347,311

[45] Aug. 31, 1982

[54] ENZYME IMMUNOASSAY FOR DETERMINING ANTIGEN SPECIFIC ANTIBODIES AND TEST KIT FOR CARRYING OUT THIS ASSAY

[75] Inventor: Hans H. Schmitz, Hamburg, Fed. Rep. of Germany

[73] Assignee: MEDAC Gesellschaft fur Klinishce Spezialpraparate mbH, Hamburg, Fed. Rep. of Germany

[21] Appl. No.: 165,395

[22] Filed: Jul. 2, 1980

[30] Foreign Application Priority Data

Jul. 28, 1979 [DE] Fed. Rep. of Germany ....... 2930706

[51] Int. Cl.³ ...................... G01N 33/54; C12Q 1/70; C12N 9/96
[52] U.S. Cl. .......................................... 435/5; 435/7; 435/177; 435/188; 435/810; 424/12; 23/230 B
[58] Field of Search ............... 424/1, 8, 12; 23/230 B; 435/5, 7, 188, 177, 810, 174

[56] References Cited

U.S. PATENT DOCUMENTS

| | | | |
|---|---|---|---|
| 3,553,310 | 1/1971 | Csizmas et al. | 435/177 |
| 3,839,153 | 10/1974 | Schuurs | 435/7 |
| 4,016,043 | 4/1977 | Schuurs et al. | 435/5 |
| 4,178,360 | 12/1979 | Cleeland | 23/230 B |
| 4,273,756 | 6/1981 | Ling et al. | 424/12 |
| 4,292,403 | 9/1981 | Duermeyer | 435/188 |
| 4,299,812 | 11/1981 | Coombes | 435/7 |

FOREIGN PATENT DOCUMENTS

2733380 2/1979 Fed. Rep. of Germany.

OTHER PUBLICATIONS

G. B. Wisdom, *Clinical Chemistry*, vol. 22, 8, pp. 1243–1255 (1976), "Enzyme Immunoassay".

Parker, *Radioimmunoassay of Biologically Active Compounds*, Prentice-Hall, N. J., (1976), p. 44.

Aurameas et al., "Coupling of Enzymes to Antibodies and Antigens", *Scand. J. Immunol. Supplement, No. 7, vol. 8 (1978)*, pp. 7–23.

Leinikki et al., "Determination of Virus-Specific IgM Antibodies by Using ELISA: Elimination of False-Positive Results with Protein A-Sepharose Absorption and Subsequent IgM Antibody Assay", *J. Lab. Clin. Med.*, vol. 92, No. 6, (1978), pp. 849–857.

Nakane et al., "Peroxidase-Labelled Antibody A New Method of Conjugation", *J. Histochem. Cytochem.*, vol. 22, No. 12, (1974), pp. 1084–1091.

*Primary Examiner*—Thomas G. Wiseman
*Attorney, Agent, or Firm*—Cushman, Darby & Cushman

[57] ABSTRACT

A highly sensitive enzyme immunoassay procedure is disclosed for determining IgM-, IgA-, IgG- and IgE-antibodies which are specific to antigens by coating a solid support with an antibody which selectively binds the antibody to be determined in a serum specimen and reacting the selectively bound antibody with an enzyme labeled microbe or antigen and then determining the enzyme activity of the reaction product as a measure of the antibody to be detected. As the antigen can be effectively labeled a relatively impure antigen can be labeled and used in high dilutions resulting in a very sensitive assay; purification by column chromatography is unnecessary. A kit for conducting the assay is also disclosed.

4 Claims, 1 Drawing Figure

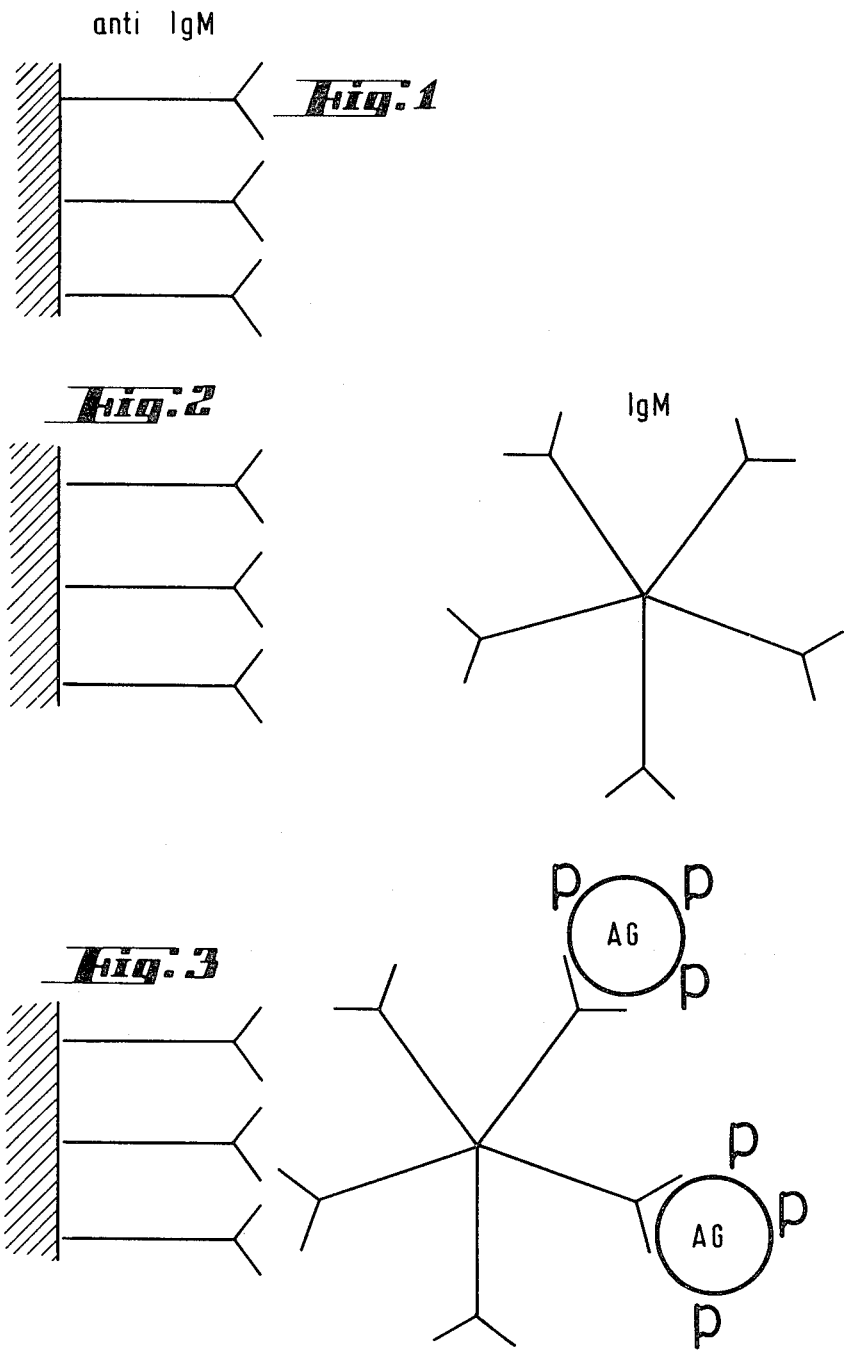

ENZYME IMMUNOASSAY FOR DETERMINING ANTIGEN SPECIFIC ANTIBODIES AND TEST KIT FOR CARRYING OUT THIS ASSAY

BACKGROUND OF THE INVENTION

The determination of antibodies against specific antigens (microbes) is of outstanding importance for making diagnoses. This is especially pertinent for antibodies of the immunoglobulin classes IgM and IgA, which are detectable in a patient's serum for a short period of time after an acute infection. The determination of specific IgM or IgA antibodies in serum specimens enables the diagnosis of acute infections.

The determination of antibodies which have been formed against specific microbes (antigens) is known. It is effected by fluoresence-, radio- or enzyme-immunoassays in such a way that an antigen is bound to an antibody and the binding reaction is determined by means of a labeled antibody. This method of operation, however, is subject to a series of deficiencies, which frequently yield incorrect results. Of importance in this context are the rheumatoid factors which react with aggregated IgG. In this case rheumatoid factor IgM is bound. Its determination, e.g. with labeled anti-IgM leads to wrong positive reactions. Wrong positive values are also obtained with anti-nucleic antibodies, since in general most commercially available antigens contain nucleic material. Furthermore many virus antigens contain Fc-receptors which likewise may lead to unspecific bondings. In addition it must be considered that especially with new-borns, which possess high concentrations of motherly IgG-concentrations, the binding of the specific IgM-antibody to the antigen may be blocked by the IgG-antibodies.

Incorrect results are also caused by the fact that labeled antibodies which are used in the known determination processes aggregate during their being labeled and form unspecific bondings with the rheumatoid factors which in the test method using labeled antibodies yield wrong positive values.

SUMMARY OF THE INVENTION

Object of the invention is to eliminate antibody-antigen bondings which are not specific.

This problem is solved in the following manner: On the one hand labeled microbes or subunits of microbes (antigens) are used for the determination of the antibodies instead of labeled antibodies, the labeling being effected with enzymes, and on the other hand the determination is carried out on a solid support which has been coated with a binding protein (antibody) which is specific to the immunoglobulins which are to be bound selectively.

When applying to this support a serum specimen which is to be tested for antibodies only the immunoglobulin class to be determined (IgM, IgA, IgG, IgE) is bound. The other constituents of the serum such as undesired immunoglobulins and albumin are removed by thoroughly washing. Thus, undesired human IgG which is contained in the serum specimen can neither react with rheumatoid factors nor can it block antigens which are used for the determination of IgM-antibodies. Using enzyme labeled antigens eliminates the hazards and complicated handling of radioisotopes. Moreover the enzymatic activity of enzyme labeled reaction products can be detected with commonly available laboratory equipment.

The labeling of antibodies with enzymes is known, see Nakane et al in The Journal of Histochemistry and Cytochemistry, Vol. 22, No. 12, S. 1084–1091 (1974). There it is also stated that the method described therein should be useful for marking proteins in general, including proteinaceous antigens. However, up to now no method of operation has become known which enables immunoreactions in an exact and reliable manner while using enzyme labeled microbes or subunits of microbes and which thus is suited for a laboratory test method. Apparently the reason therefor is that with enzyme labeled microbes or antigens there are by far more possibilities to react with the components of the physiological liquid to be tested than with radiolabeled antigens.

Surprisingly, it has now been found that antigens can be marked in an outstanding effective manner, if the enzyme is bound to the antigen at an alkaline pH of 9.3 in the presence of such an amount of one or several alkaline buffer materials that even after the dilution of the formed enzyme conjugate and during the reaction thereof with the antibody to be determined an alkaline pH of about 8.7 is maintained. If necessary this alkaline pH can be adjusted by further addition of an alkaline material. The very effective marking allows that even a relatively impure antigen can be marked and furthermore, that the marked antigen can be used in a rather high dilution of up to 1:400 which greatly favours the sensitivity of the laboratory test method. The hitherto necessary purification of the enzyme-conjugate by column chromatography to remove nonreacted substances is as unnecessary as is the blocking of free $\epsilon$- and $\alpha$-amino groups in the protein materials to prevent undesired reactions. The effective marking of the antigen and the smooth course of the binding reaction between the labeled antigen and the antibody to be determined is all the more surprising since the conditions under which according to the invention the coupling reaction between the enzyme and the antigen as well as the binding reaction between the labeled antigen and the antibody are effected are physiologically unusual and thus were not obvious to the expert. In addition, non-specific bondings of the labeled antigens to the solid support are essentially reduced, if the labeled antigen is applied in a dilution which contains calf-serum, especially serum of new-born calves and a non-ionic detergent, such as polyoxyethylene sorbitane laurate. The non-ionic detergent has the additional effect that it facilitates the removal of unbound material by washing. Proceeding in this manner yields a minimum of background reactions with negative control specimens.

The test method according to the invention which is of outstanding sensitivity is schematically shown in the drawing. In it demonstrates:

FIG. 1 the solid support coated with the class specific anti-antibody, i.e. anti-IgM.

FIG. 2 the specific antibody IgM, which is to be detected in the serum specimen and which is selectively bound to the coated solid support.

FIG. 3 the binding reaction between the anti-antibody, the antibody to be detected and peroxidase-labeled antigen = |—anti-IgM:IgM:Ag (peroxidase).

It is advantageous to use for the determination of the antibody a disintegration piece of the microbe, i.e. an antigen, preferably an antigen which has been freed from nucleic components which may produce undesired antibody-reactions.

Due to the elimination of reactions between non class specific antibodies with the antigens and the effective marking of the antigens the test method according to the invention is highly specific and highly sensitive. The specific antibodies to be determined can be detected in a dilution of up to 1:1,000,000 though negative serum specimens show no reaction in a dilution of only 1:100. A further advantage of the claimed test method consists therein that in comparison to test methods using labeled antibodies which require three steps, only two steps are necessary, so that the claimed method is simpler and faster.

Suitable solid supports for proteins which bind class specific immunoglobulins are known. Examples therefor are cellulose compounds, dextranes, synthetic polymers, such as polystyrene and polyvinylchloride which can be used in the form of particles of different size, such as grains, plates, rods or strips. The proteins can be bound on these supports by known physical or chemical methods.

Suitable enzymes for marking the microbes or antigens are e.g. phosphatases and peroxidases. The particular enzyme is selected depending on its properties, e.g. according to its binding activity and its easy determination. Enzymes which catalyze a conversion in which coloured reaction components are participating are preferred, since they allow simple colorimetric determinations which can be automated.

The enzyme can be bound to the antigen by means of covalent bondings between the antigen protein and the enzyme or via groups which can react with reactive groups of the enzyme or via introduced groups which enable a reaction between the antigen and the enzyme, provided the properties of the bound antigen and the activity of the enzyme are not affected thereby.

The invention comprises also a test-kit for carrying out the process according to the invention which involves e.g.

(a) a solid support, e.g. a microtiter plate which is coated with a binding protein for a specific immunoglobulin (antibody);
(b) an enzyme labeled antigen and
(c) a substrate for the enzyme reaction.

The following example illustrates an embodiment of the invention. The invention is of course not limited to this specific embodiment but comprises modifications of the inventive teaching which are within the expert's knowledge.

EXAMPLE

Preparation of purified enzyme-labeled antigen

A Preparation of purified antigen

For labeling virus antigens virus-infected cells (tissue culture) are sedimented at 3000 rotations per minute for 5 minutes.

The supernatant is decanted and the cells are washed once with phosphate-buffered saline (PBS). Thereafter the sediment is taken up in 1 ml of distilled water and 1% non-ionic detergent solution (NP 40). Then it is placed in an ice-bath and subjected to sonic waves 10 times, 3 seconds each (Branson Sonfier, output control 7, microtip) for disintegration. Thereafter rough cell structures are removed by centrifuging 5 minutes at 3000 rotations per minute. The supernatant is applied on a pad of 30% dextrane-T10 (Pharmacia) in a TE-buffer (0.01 M TRIS (tris-(hydroxyethyl)-aminoethane)-HCL+0.001 M EDTA (ethytenediamine tetraacetic acid), pH 7.4; supernatant/-dextrane 1:9) and sedimented for 1 to 8 hours at 35,000 up to 60,000 rotations per minute, depending on the virus antigen (Beckman centrifuge, SW 41). The sediment is taken up in 1 ml of dist. water and again subjected to sonic waves 3 times, 5 seconds each in an ice-bath (conditions as above). Thereafter the protein content is determined according to the method of Lowry. It should amount from 0.5 to 1 mg/ml.

B Enzyme-labeling the antigen (1) Activation of the peroxidase 4 mg horseradish-peroxidase (Sigma) are taken up in 1 ml of dist. water. Then 0.2 ml 1M Na $IO_4$ (21 mg/ml dist. water) are added. The solution is incubated for 20 minutes at 20° C. and should turn to olive-green during this period of time. Thereafter it is dialyzed over night against 0.001 M sodium acetate buffer of pH 4.4.

(2) Coupling the peroxidase to the antigen

To 1 ml purified virus with a protein content of 0.5–1 mg/ml the activated peroxidase is given in the weight ratio peroxidase/virus-protein of 2 mg/1 mg immediately after the addition of 0.1 ml sodium carbonate buffer (0.5–1 M; pH 9,3).

Subsequently it is incubated at 4° C. for 2.5 hours. Thereafter a freshly prepared solution of 4 mg/ml Na $BH_4$ in the ratio 1/20 (V/V) is added and it is again incubated at 4° C. for 2 hours. The formed conjugate is tested in different dilutions in phosphate-buffered saline+5% calf serum against one serum containing specific IgM-antibodies and another one containing no such antibodies (serum dilution 1:100). The optimal antigen dilution can then be frozen at-70° C. or be lyophilized together with 5% calf serum.

In the aforesaid manner Cytomegalo virus, various other Herpes viruses, Rubella virus and Hepatitis virus have been successfully marked with peroxidase.

Preparation of the anti-IgM coated support for selectively binding the antibodies to be determined As solid phase flexible PVC-microtiter plates (Dynatech) with 96 wells are used. Dilutions of purified rabbit antibody specific for $\mu$-chains of human Ig but also for e.g. $\alpha$-, $\gamma$- or $\epsilon$-chains of human Ig (10 ml protein/ml) are prepared in the ratio 1:300 in phosphate-buffered saline and are added with 1 mg/ml $NaN_3$. 0.1 ml thereof are filled in each well and the plate is incubated in a moist chamber at 20° C. After 24 hours in each well 10% calf serum, likewise together with 1 mg/$NaN_3$ are added and it is again incubated for 24 hours under the same conditions. After 10 days at 4° C. the plates can be washed with phosphate-buffered saline and after a final washing with distilled water they can be dried, then sealed air-tight with a transparent sheet and stored at 4° C. for at least 6 months.

Determination method

After the sheet has been removed the plate is washed. In doing this it is shaken out and filled with phosphate-buffered saline which contains 0.05% polyoxyethylene sorbitane laurate (Tween 20). After 60 seconds the plate is emptied. This procedure is repeated 5 times. Finally the plate is briefly washed two times with pure phosphate-buffered saline to prevent the formation of bubbles. Thereafter the plate is knocked out overhead on an absorbing support but the plate must by no means become dry. This washing cycle is repeated after every working operation. The serum specimens are diluted in phosphate-buffered saline which contains 1 mg/ml NaN$_3$ and possibly 0.01% Phenol Red to make it more visible and then pipetted in the wells of the coated plate and incubated in a moist chamber for two hours at 20° C. As controls two positive and two negative sera with known antibody titers are used. Then the plate is washed, the lyophilized antigen, dissolved in phosphate-buffered saline and 0.5% polyoxyethylene sorbitane laurate (Tween 20) of pH 8.7 is added and it is incubated in the moist chamber at 20° C. for two hours. After this step the plate is washed and then it is dyed.

Staining 10 mg o-phenylene diamine are dissolved in 10 ml phosphate buffer (0.1 M, pH 6) and 0.001% H$_2$O$_2$. This solution must be freshly prepared before the staining and must not be exposed to direct light. 50 μl are given in each well. After 5 to 6 minutes the reaction is stopped by the addition of 0,1 ml and 2 M H$_2$SO$_4$. The evaluation is effected with the naked eye or photometrically at 490 nm.

I claim:

1. An enzyme immunoassay method for determining the presence of antibodies which are specific to antigens using enzyme-labelled viruses or microbial cells in an antibody-antigen reaction, said method comprising the sequential steps of:

(a) coating a solid support with antibodies which selectively bind IgM, IgA, IgG or IgE antibodies which are to be determined in a serum specimen;

(b) contacting the coated support with the serum specimen containing the antibodies to be determined which antibodies are selectively bound by the antibodies of the coated support;

(c) removing unbound components of the specimen from the support;

(d) reacting the selectively bound antibodies at pH about 8.7 with a solution containing: carbonate buffer, calf serum, non-ionic detergent and a peroxidase conjugate of a virus or a microbial cell which conjugate is highly specific to the bound antibody and which conjugate has been prepared by periodate coupling the virus or microbial cell in a carbonate buffer of pH about 9.3 and of high mg/ml virus or microbial cell concentration; and thereafter (e) determining the enzyme activity of the reaction product as a measure of the presence of the antibodies to be determined.

2. The method according to claim 1 wherein the enzyme is coupled to the microbe or antigen in a ratio that contains per ml about 1.5 mg enzyme and about 1 ml microbe or antigen.

3. The method according to claim 1 wherein the solid support is coated with purified antibodies which selectively bind IgM- or IgA-antibodies.

4. The method according to claim 1 wherein an enzyme-labeled antigen is used which is substantially free from nucleic materials.

* * * * *